United States Patent [19]
Sommer et al.

[11] Patent Number: 5,948,757
[45] Date of Patent: Sep. 7, 1999

[54] HIGH DOSE IGF-1 THERAPY

[75] Inventors: Andreas Sommer, Danville; Jerome A. Moore, San Mateo; Steven Adams, Sunnyvale, all of Calif.

[73] Assignee: Celtrix Pharmaceuticals, Inc., Santa Clara, Calif.

[21] Appl. No.: 08/609,650

[22] Filed: Mar. 1, 1996

[51] Int. Cl.$^6$ .......................... A61K 38/00; A61K 38/28
[52] U.S. Cl. ............................... 514/12; 514/3; 530/303
[58] Field of Search ......................... 514/12, 3; 530/303

[56] References Cited

U.S. PATENT DOCUMENTS

| | | | |
|---|---|---|---|
| 5,126,324 | 6/1992 | Clark et al. | 514/12 |
| 5,187,151 | 2/1993 | Clark et al. | 514/3 |
| 5,202,119 | 4/1993 | Clark et al. | 424/88 |

FOREIGN PATENT DOCUMENTS

| | | |
|---|---|---|
| 0 128 733 | 12/1984 | European Pat. Off. . |
| WO 95/04076 | 2/1995 | WIPO . |

OTHER PUBLICATIONS

Malozowski et al. (1994) "Risks and Benefits of Insulin–like Growth Factor," *Ann. Internal Med.* 121(7):549.
Cioffi et al. (1994) "Insulin–Like Growth Factor–1 Lowers Protein Oxidation in Patients with Thermal Injury," *Annals of Surgery* 220(3):310–319.
Takano et al. (1990) "Effects of sc Administration of Recombinant Human Insulin–Like Growth Factor I (IGF–I) on Normal Human Subjects," *Endocrinol. Japon.* 37(2):309–317.
Klinger et al. (1993) "Acute Effects of IGF–1 in Patients with Laron Syndrome and Normal Subjects," *Pediatr. Adolesc. Endocrinol.* 24:221–225.
Ebling et al. (1995) "Short–Term Effects of Recombinant Human Insulin–Like Growth Factor I on Bone Turnover in Normal Women," *J. Clin. Endocrinol. Metabolism* 77(5):1384–1387.
Miller et al. (1994) "Effects of IGF–I on Renal Function in End–Stage Chronic Renal Failure," *Kidney International* 46:201–207.
Thompson et al. (1995) "The Effects of Recombinant Human Insulin–Like Growth Factor–I and Growth Hormone on Body Composition in Ederly Women," *J. Clin. Endocrinol. Metabolism* 80(6):1845–1852.
Lieberman et al. (1994) "Anabolic Effects of Recombinant Insulin–Like Growth Factor–I in Cachectic Patients with the Acquired Immunodeficiency Syndrome," *J. Clin. Endocrinol.* 78(2):404–410.
Laron et al. (1991) "Biochemical and Hormonal Changes Induced by One Week of Administration of rIGF–I to Patients with Laron Type Dwarfism," *Clin. Endocrinol.* 35:145–150.
Grinspoon et al. (1995) "Effects of rhIGF–I Administration on Bone Turnover During Short–Term Fasting," *The American Society of Clinical Investigation, Inc.* 96:900–906.

Guler et al.(1987) "Short–Term Metabolic Effects of Recombinant Human Insulin–Like Growth Factor I In Healthy Adults," *New England J. Medicine* 317:137–140.
Jabri et al. (1994) "Adverse Effects of Recombinant Human Insulin–Like Growth Factor I in Obese Insulin–Resistant Type II Diabetic Patients," *Diabetes* 43:369–274.
Stong et al. (1993) "Effects of Multiple Subcutaneous Doses of rhIGF–1 on Total and Free IGF–1 Levels and Blood Glucose in Humans," *Ann. New York Acad. Sci.* 692:317–320.
Adams, S., et al., "Protection from hypoglycemic response to IGF–I by administration of IGF–I with its binding protein IGFBP–3 in the rat and monkey" The Endocrine Society, 77th Annual Meeting, Jun. 14–17, 1995, Washington, D.C., p. 186.
Blum et al., "Plasma IGFBP–3 levels as clinical indicators" *Modern Concepts in Insulin–Like Growth Factors*, (1991) E.M. Spencer, ed., Elsevier, New York, pp. 381–393.
Zapf et al., "Intravenously injected insulin–like growth factor (IGF) I/IGF binding protein–3 complex exerts insulin–like effects in hypophysectomized, but not in normal rats" *Clinical Investigation* (1994) 95:179–186.
Baxter, "Circulating levels and molecular distribution of the acid–labile ($\alpha$) subunit of the high molecular weight insulin–like growth factor–binding protein complex" *J. Clin. Endocrinol.* (1990) 70:1347–1353.
Rinderknecht et al., "Polypeptides with nonsuppressible insulin–like and cell–growth promoting activities in human serum: Isolation, chemical characterization, and some biological properties of forms I and II" *Proc. Natl. Acad. Sci. USA* (1976) 73:2365–2369.
Baxter et al., "Growth hormone–dependent insulin–like growth factors (IGF) binding protein from human plasma differs from other human IGF binding proteins" *Biochem. Biophys. Res. Comm.* (1986) 139:1256–1261.
Sommer et al., "Molecular genetics and actions of recombinant insulin–like growth factor binding protein–3" *Modern Concepts of Insulin–Like Growth Factors* (1991) E.M. Spencer, ed., Elsevier, New York, pp. 715–728.
Clemmons et al., "Uses of human insulin–like growth factor–1 in clinical conditions" *J. Clin. Endocrinol. Metabol.* (1994) 79:4–6.
Clark et al., "Insulin–like growth factor I stimulation of lymphopoiesis" *J. Clin. Invest.* (1993) 92:540–548.
Delany et al., "Cellular and clinical perspectives on skeletal insulin–like growth factor I" *J. Cell. Biochem.* (1994) 55:328–333.
Steenfos, "Growth factors and wound heeling" *Scand. J. Plast. Reconstr. Surg. Hand Surg.* (1994) 28:95–105.

(List continued on next page.)

*Primary Examiner*—Cecilia J. Tsang
*Assistant Examiner*—Anish Gupta
*Attorney, Agent, or Firm*—Morrison&Foerster LLP

[57] ABSTRACT

The present invention involves a method for providing high dose IGF-I therapy by administering a complex of IGF-I and IGFBP-3. The IGF-I/IGFBP-3 complex may be given at unexpectedly high doses without inducing IGF-I-related side effects.

2 Claims, 2 Drawing Sheets

OTHER PUBLICATIONS

Lewis et al., "Insulin–like growth factor I: Potential for treatment of motor neuronal disorders" *Exp. Neurol.* (1993) 124:73–88.

Lieberman et al., "Effects of recombinant human insulin–like growth factor–I (rhIGF–I) on total and free IGF–I concentrations, IGF–binding proteins and glycemic response in humans" *J. Clin. Endocrinol. Metab.* (1992) 75:30–36.

Guler et al., "Short–term metabolic effects of recombinant human insulin–like growth factor I in healthy adults" *New Engl. J. Med.* (1987) 317:137–140.

Goth, "Drug absorption and distribution" *Medical Pharmacology* 13th edition, (1992) Clark, W. G. et al., eds., *Mosby Year Book*, St. Louis, pp. 33–34.

Goodman et al., *The Pharmacological Basis of Therapeutics*, Eighth edition, (1990) Gilman et al., eds., Pergamon Press, New York. The title page and table of contents are included herewith.

Baxter et al., "Structure of the $M_r$ 140,000 growth hormone–dependent insulin–like growth factor binding protein complex: Determination by reconstitution and affinity–labeling" *Proc. Natl. Acad. Sci. USA* (1989) 86:6898–6902.

Baxter et al., "Regulation of the insulin–like growth factors and their binding proteins by glucocorticoid and growth hormone in nonislet cell tumor hypoglycemia" *J. Clin. Endocrinol. Metab.* (1995) 80:2700–2708.

Baxter et al., "Purification and characterization of the acid–labile subunit of rat serum insulin–like growth factor binding complex" *Endocrinol.* (1994) 134:848–852.

Davies et al., "Physiological parameters in laboratory animals and humans" *Pharm. Res.* (1993) 10:1093–1095.

Bagi et al., "Benefit of systemically administered rhIGF–I and rhIGF–I/IGFBP–3 on cancellous bone in ovariectomzed rats" *J. Bone Mineral Res.* (1994) 9:1301–1311.

Bagi et al., "Systemic administration of rhIGF–I or rhIGF–I/IGFBP–3 increases cortical bone and lean body mass in ovariectomized rats" *bone* (1995) 16:263S–269S.

Bagi et al., "Treatment of ovariectomized rats with the complex of rh1GF/IGFBP–3 increases cortical and cancellous bone mass and improve structure in the femoral neck" *Calcif. Tissue Int.* (1995) 57:40–46.

Bengtsson et al., "Treatment of adults with growth hormone (GH) deficiency with recombinant human GH" *J. Clin. Endocrinol.* (1993) 76:309–317.

Ross et al., "Critically ill patients have high basal growth hormone levels with attenuated oscillatory activity associated with low levels of insulin–like growth factor" *Clin Endocrinol.* (1978) 35:47–54.

Hintz et al., "Plasma somatomedin and growth hormone values in children with protein–calorie malnutrition" *J. Pediatr.* (1978) 92:153–156.

Dahn et al., "Insulin–like growth factor I production is inhibited in human sepsis" *Arch. Surg.* (1988) 123:1409–1414.

Miell et al., "Administration of human recombinant insulin–like growth factor–I to patients following major gastrointestinal surgery", *Clin. Endocrinol.* (1992) 37:542–551.

Cioffi et al., "Insulin–like growth factor–1 lowers protein oxidation in patients with thermal injury" *Ann. Surg.* (1994) 220:310–319.

Lieberman et al., "Anabolic effects of recombinant insulin–like growth factor–I in cachectic patients with acquired immunodeficiency syndrome" *J. Clin. Endocrinol. Metabol.* (1994) 78:404–410.

*The Merck Manual of Diagnosis and Therapy*, (1992) 16th ed., Berkow, R., ed., Merck Research Laboratories, Rahway, NJ. The title page and table of contents are included herewith.

Malozowski et al., "Risks and benefits of insulin–like growth factor" *Ann. Int. Med.* (1994) 121:549.

"Current Emergency Diagnosis and Treatment", (1992) 4 ed., Saunders et al., eds. *Lange Medical Publications*. The title page and table of contents are included herewith.

Jabri et al., "Adverse effects of recombinant human insulin–like growth factor I in obese insulin–resistant Type–II diabetic patients" *Diabetes* (1994) 43:369–374.

Ogle et al., "Renal effects of growth hormone. II. Electrolyte homeostasis and body composition",*Pediatr. Nephrol.* (1992) 6:483–489.

Cohn et al., "Carpal tunnel syndrome and gynaecomastia during growth hormone treatment of elderly men with low circulating IGF–I concentrations", *Clin. Endocrinol.* (1992) 39:417–425.

Bagi et al., "Systemic Administration of rhIGF–I or rhIGF–I/IGFBP–3 Increases Cortical Bone and Lean Body Mass in Ovariectomized Rats" *Bone* (1995) 16(4 Suppl):253S–269S.

Zapf et al., J. Clin. Invest., vol. 95, Jan. 1995, pp. 179–186 (1995).

HIGH DOSE IGF-1 THERAPY

FIELD OF THE INVENTION

The invention relates generally to the treatment of humans with insulin like growth factor complexed to insulin like growth factor binding proteins, and particularly to the treatment of humans with insulin like growth factor I complexed to insulin-like growth factor binding protein-3.

BACKGROUND

Growth factors are polypeptides which stimulate a wide variety of biological responses (e.g., DNA synthesis, cell division, expression of specific genes, etc.) in a defined population of target cells. A variety of growth factors have been identified, including transforming growth factor β1 (TGF-β1), TGF-β2, TGF-β3, TGF-β4, TGF-,β5, epidermal growth factor (EGF), platelet-derived growth factor (PDGF), fibroblast growth factor (FGF), insulin-like growth factor-I (IGF-1) and IGF-II.

IGF-I and IGF-II are related in amino acid sequence and structure, with each polypeptide having a molecular weight of approximately 7.5 kilodaltons (kD). IGF-I mediates the major effects of growth hormone, and thus is the primary mediator of growth after birth. IGF-I has also been implicated in the actions of various other growth factors, since treatment of cells with such growth factors leads to increased production of IGF-I. In contrast, IGF-II is believed to have a major role in fetal growth. Both IGF-I and IGF-II have insulin-like activities (hence their names), and are mitogenic (stimulate cell division) for the cells in neural tissue, muscle, reproductive tissue, skeletal tissue and a wide variety of other tissues.

Unlike most growth factors, the IGFs are present in substantial quantity in the circulation, but only a very small fraction of this IGF is free in the circulation or in other body fluids. Most circulating IGF is bound to an IGF-binding protein called IGFBP-3. IGF-I may be measured in blood serum to diagnose abnormal growth-related conditions, e.g., pituitary gigantism, acromegaly, dwarfism, various growth hormone deficiencies, etc. Although IGF-I is produced in many tissues, most circulating IGF-I is believed to be synthesized in the liver.

Almost all IGF circulates in a non-covalently associated ternary complex composed of IGF-I or IGF-II, IGFBP-3, and a larger protein subunit termed the acid labile subunit (ALS). This ternary complex is composed of equimolar amounts of each of the three components. ALS has no direct IGF binding activity and appears to bind only to the IGF/IGFBP-3 binary complex. The ternary complex of IGF+ IGFBP-3 +ALS has a molecular weight of approximately 150 Kd. This ternary complex is alleged to function in the circulation "as a reservoir and a buffer for IGF-I and IGF-II preventing rapid changes in the concentration of free IGF" (Blum et al., 1991, "Plasma IGFBP-3 Levels as Clinical Indicators" in Modem Concepts in Insulin-Like Growth Factors, E. M. Spencer, ed., Elsevier, New York, pp. 381–393). The ternary complex is also believed to play an important role in the prevention of hypoglycemia due to high doses of IGFI, by binding IGF-I/IGFBP-3 complex and restricting its distribution (Zapf et al., 1994, "Intravenously Injected Insulin-like Growth Factor (IGF) I/IGF Binding Protein-3 Complex Exerts Insulin-like Effects in Hypophysectomized, but Not in Normal Rats", Clinical Investigation 95: 179–186). ALS is growth hormone-dependent, so hypophysectomized rats and other subjects with insufficient levels of growth hormone have little to noALS (Baxter, 1990, 1990, "Circulating Levels and Molecular Distribution of the Acid-labile (α) Subunit of the High Molecular Weight Insulin-like Growth Factor-Binding Protein Complex" J Clin. Endocrinol. 70(5): 1347–1353).

Nearly all of the IGF-I, IGF-II and IGFBP-3 in the circulation is in complexes, so very little free IGF is detectable. Moreover, a high level of free IGF in blood is undesirable. High blood levels of free IGF lead to serious hypoglycemia, due to the insulin-like activities of IGF, as well as other adverse side effects. In contrast to the IGFs and IGFBP-3, there is a substantial pool of free ALS in plasma which assures that IGF/IGFB-3 complex entering the circulation immediately forms the ternary complex. However, it is believed that saturating free ALS by administration of high levels of IGF-I/IGFBP-3 will also lead to hypoglycemia (Zapf et al., ibid).

IGFBP-3 is the most abundant IGF binding protein in the circulation, but at least five other distinct IGF binding proteins (IGFBPs) have been identified in various tissues and body fluids. Although these proteins bind IGFs, they each originate from separate genes and have distinct amino acid sequences. Thus, the binding proteins are not merely analogs or derivatives of a common precursor. Unlike IGFBP-3, the other IGFBPs in the circulation are not saturated with IGFs. None of the IGFBPs other than IGFBP-3 can form the 150 Kd ternary complex with IGF-I and ALS.

IGF-I and IGFBP-3 may be purified from natural sources or produced by recombinant means. For instance, purification of IGF-I from human serum is well known to the art (Rinderknecht et al., 1976, Proc. Natl. Acad. Sci, (USA) 73: 2365–2369). Production of IGF-I by recombinant processes is shown in EP 0,128,733, published in December of 1984. IGFBP-3 may be purified from natural sources using a process such as that shown in Baxter et al., (1986, "Growth Hormone-Dependent Insulin-Like Growth Factors (IGF) Binding Protein from Human Plasma Differs from Other Human IGF Binding Proteins", Biochem Biophys. Res, Comm, 139: 1256–1261). IGFBP-3 may be synthesized by recombinant organisms as discussed in Sommer et al. (1991, "Molecular Genetics and Action of Recombinant Insulin-Like Growth Factor Binding Protein-3", in Modem Concepts of Insulin-Like Growth Factors, E. M. Spencer, ed., Elsevier, New York, pp. 715–728). This recombinant IGFBP-3 binds IGF-I in a 1:1 molar ratio.

Studies with IGF-I have suggested its utility in treating a wide variety of indications. Clemmons and Underwood (1994, "Uses of Human Insulin-like Growth Factor-I in Clinical Conditions" J Clin. Endocrinol. Metabol. 79(1): 4–6) have suggested that IGF-I may be useful for the treatment of catabolic states, such as can arise due to trauma, severe burns, and major surgery. Clemmons and Underwood (supra) also suggest the utility of IGF-I in the treatment of acute and chronic renal disorders. IGF-I may be useful for the treatment of lymphopoietic disorders (Clark et al., 1993, "Insulin-like Growth Factor I Stimulation of Lymphopoiesis" J Clin. Invest. 92: 540–548). IGF-I has also been suggested as potentially useful in the treatment of bone disorders, such as osteoporosis, as well as wound healing and peripheral nerve disorders (Delany et al., 1994, "Cellular and Clinical Perspectives on Skeletal Insulin-like Growth Factor I" J. Cell. Biochem. 55(3): 328–333; Steenfos, 1994, "Growth Factors and Wound Healing" Scand J Plast. Reconstr. Surg. Hand Surg. 28(2): 95–105; Lewis et al., 1993, "Insulin-like Growth Factor I: Potential for Treatment of Motor Neuronal Disorders" Exp. Neurol. 124(1): 73–88).

IGF-I, when administered alone, can give rise to multiple deleterious side effects. The most commonly cited side effect of IGF-I administration is the induction of hypoglycemia. IGF-I induces significant hypoglycemia (significant hypoglycemia is normally defined as a decrease in blood glucose of 30% or more) in humans at doses of 30 µg/kg by intravenous administration and 100 µg/kg by subcutaneous administration (Lieberman et al., 1992, "Effects of Recombinant Human Insulin-like Growth Factor-I (rhIGF-I) on Total and Free IGF-I Concentrations, IGF-Binding Proteins, and Glycemic Response in Humans", *J. Clin. Endocrinol. Metab.* 75(1): 30–36; Guler et al., 1987, "Short-term Metabolic Effects of Recombinant Human Insulin-like Growth Factor I in Healthy Adults", *New England J. Med.* 317(3): 137–140). Other side effects include hypophosphatemia, which can cause muscle seizures and cardiac arrhythmia, and changes in sodium excretion, which can lead to edema.

The activities of the IGF-I/IGFBP-3 complex have been less extensively studied. In wound healing, topical administration of IGF-I/IGFBP-3 complex to rat and pig wounds is significantly more effective for promoting wound healing than administration of IGF-I alone (Sommer et al., supra).

Some studies have been performed using systemically administered IGF-I/IGFBP-3 complex, although usually at low doses. Zapf et al. (supra) gave normal and hypophysectomized rats a 4 mg/kg IV bolus of IGF-I/IGFBP-3 complex. This dose induced significant hypoglycemia in hypophysectomized rats, which are deficient in growth hormone and growth hormone-dependent proteins (such as ALS), but not normal rats. Sommer et al. (supra) gave a greater dose of IGF-I/IGFBP-3 complex to hypophysectomized rats, 40 mg/kg. This dose, which was administered by subcutaneous bolus injection, induced significant hypoglycemia (50% reduction in blood glucose). Although the dose given by Sommer et al. appears to be significantly greater than that given by Zapf et al., Sommer used a different route of administration (subcutaneous). Subcutaneous administration normally results in a lower and delayed peak concentration in the blood, particularly with large protein drugs (for example, see *Goth's Medical Pharmacology*, 13th edition, Clark, W. G., Brater, D. C., and Johnson, A. R., eds. Mosby Year Book, St. Louis, 1992 and *Goodman and Gilman's The Pharmacological Basis of Therapeutics*, Eighth edition, Gilman, A. G., Rall, T. W., Nies, A. S., and Taylor, P., eds., Pergamon Press, New York, 1990).

In addition to testing IGF-I and IGF-I/IGFBP-3 complex, Zapf also forwarded a model for explaining why IGF-I/IGFBP-3 complex causes a lower degree of hypoglycemia compared to IGF-I alone. The Zapf model is the first and only model that can be used to make quantitative predictions as to the dose of IGF-I/IGFBP-3 complex that will cause hypoglycemia. The Zapf model predicts that IGF-I/IGFBP-3 complex bound in the ternary complex with ALS is non-hypoglycemic, but IGF-LIGFBP-3 complex in the 40 kD complex (i.e., not bound to ALS) can cause hypoglycemia. IGF-I alone is hypoglycemic because there is no excess IGFBP-3 to form the 40 kD complex, and thus free IGF-I cannot form the 150 kD ternary complex (Baxter and Martin, 1989, "Structure of the $M_r$ 140,000 Growth Hormone-dependent Insulin-like Growth Factor Binding Protein Complex: Determination by Reconstitution and Affinity-labeling" *Proc. Natl. Acad Sci. USA* 86: 6898–6902)., The Zapf model predicts that adding enough IGF-I/IGFBP-3 complex to saturate ALS in the blood would lead to hypoglycemia. This model is supported by Baxter et al., who suggest that low ALS levels are cause of hypoglycemia in patients with nonislet cell tumors (1995, "Regulation of the Insulin-like Growth Factors and Their Binding Proteins by Glucocorticoid and Growth Hormone in Nonislet Cell Tumor Hypoglycemia" *J. Clin. Endocrinol. Metabol.* 80(9): 2700–2708).

The model disclosed in Zapf may be used to calculate the dose at which IGF-I/IGFBP-3 complex is expected to induce hypoglycemia. This calculation requires the determination of (a) the amount of IGF-I/IGFBP-3 complex required to bind all the free ALS in the blood and (b) the amount of IGF-I/IGFBP-3 complex that is the molar equivalent of the dose of free IGF-I that induces hypoglycemia. These two numbers are added together to find the dose of IGF-I/IGFBP-3 complex that is expected to induce hypoglycemia.

ALS levels, both total and free ALS, have been measured in humans and rats (Baxter, supra; Baxter and Dai, 1994, "Purification and Characterization of the Acid-labile Subunit of Rat Serum Insulin-like Growth Factor Binding Complex" Endocrinol. 134(2): 848–852). In rats, total ALS is reported to be 42 µg/ml in blood (ALS is limited to the vascular space due to its large size). Of that 42 µg/ml, 33.6 µg/ml (80%) of the ALS is free (i.e., not bound to the IGFI/IGFBP-3 complex) (Baxter and Dai, supra). In normal humans, total ALS is 24.2 µg/ml, with one third, or 8 µg/ml, of the total as free ALS. The amount of IGF-I/IGFBP-3 complex required to bind the free ALS is the molar equivalent of the free ALS; approximately 16.5 µg/ml in the rat and 4 µg/ml in the human. These numbers are then multiplied by the blood volumes of rats and humans, respectively, to yield the quantity of IGF-I/IGFBP-3 complex required to bind all of the free ALS (total blood volume is 54 ml/kg in rats, 74.3 ml/kg in humans (Davies and Morris, 1993, "Physiological Parameters in Laboratory Animals and Humans", *Pharm. Res.* 10(7): 1093–1095). Thus, the amount of IGF-I/IGFBP-3 complex required to bind all of the free ALS is 891 µg/kg in rats and 300 µg/kg in humans. Significant hypoglycemia is induced by IV IGFI at 0.8 mg/kg in rats (Zapf et al., supra) and 0.03 mg/ml in humans Lieberman et al., supra). The molar equivalent amounts of IGF-I/IGFBP3 complex are 4 mg/kg and 0.15 mg/kg, respectively. Thus, the amount of IGF-I/IGFBP-3 complex expected to produce hypoglycemia, administered IV, is 4.9 mg/kg in rats and 0.45 mg/kg in humans.

It would be desirable to give doses of IGF-I/IGFBP-3 complex that are even greater than the doses that are predicted to cause hypoglycemia. This is because of the expected greater efficacy of a higher dose. Studies with IGF-I/IGFBP-3 complex show a dose-response relationship, but show no signs of a plateau in the response to increasing amounts of the complex, suggesting that greater doses would lead to increased efficacy (Bagi et al., 1994, "Benefit of Systemically Administered rhIGF-I and rhIGF-I/IGFBP-3 on Cancellous Bone in Ovariectomized Rats", *J Bone Mineral Res.* 9(8): 1301–1311; Bagi et al., 1995, "Systemic Administration of rhIGF-I or rhIGF-I/IGFBP-3 Increases Cortical Bone and Lean Body Mass in Ovariectomized Rats", Bone 16(4 suppl.): 263S–269S; Bagi et al., 1995, "Treatment of Ovariectomized Rats with the Complex of rhIGF-I/IGFBP-3 Increases Cortical and Cancellous Bone Mass and Improves Structure in the Femoral Neck". *Calcif Tiss. Int.* 57: 40–46).

Accordingly, there exists in the art a need for a method for providing high dose IGF-I or IGF-I/IGFBP-3 complex therapy.

BRIEF SUMMARY OF THE INVENTION

The present invention provides a method for providing high dose IGF-I therapy without inducing the side effects of IGF-I. The inventors have found that a complex of IGF-I and IGFBP-3 may be administered at surprisingly high levels without inducing IGF-I-related side effects.

In one aspect, the invention provides a method of providing high dose IGF-I therapy without inducing hypoglycemia by administering IGF-I/IGFBP-3 complex by intravenous, intramuscular, intraperitoneal, or subcutaneous routes.

In another aspect, the invention provides a method for providing high dose IGF-I therapy without inducing hypoglycemia in a subject with insufficient levels of growth hormone or growth hormone resistance by administering IGF-I/IGFBP-3 complex by intravenous, intramuscular, intraperitoneal, or subcutaneous routes.

DISCLOSURE OF THE INVENTION

Figure 1:
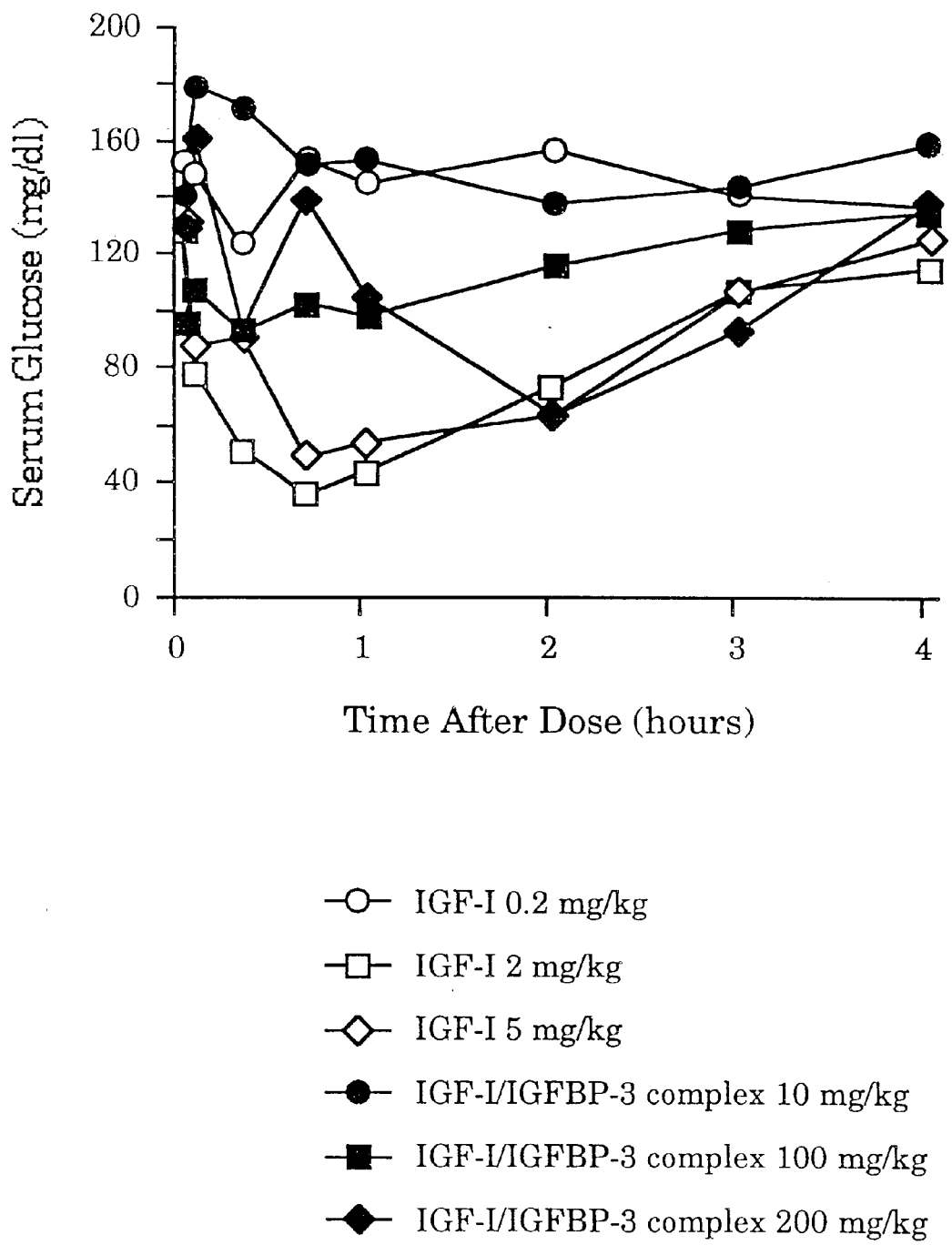
FIG. 1 shows the effects of IGF-I and IGF-I/IGFBP-3 on serum glucose in rats. Open circles indicate 0.2 mg/kg rhIGF-I; open squares indicate 2 mg/kg rhIGF-I; open diamonds indicate 5 mg/kg rhIGF-I; filled circles indicate 10 mg/kg rhIGF-I/IGFBP-3 complex (molar equivalent of 2 mg/kg rhIGF-I); filled squares indicate 100 mg/kg rhIGF-I/IGFBP-3 complex (molar equivalent of 20 mg/kg rh1 GF-I); filled diamonds indicate 200 mg/kg rhIGF-I/IGFBP-3 complex (molar equivalent of 40 mg/kg rhIGF-1).

The invention relates high dose IGF-I therapy, by administering an unexpectedly large dose of a complex of IGF-I and IGFBP-3. Applicants have found that the IGF-I/IGFBP-3 complex can protect the subject from the known adverse effects of IGF-I alone, and also be used to deliver a surprisingly large dose to the subject.

Protection from IGF-I-induced hypoglycemia by administration of IGF-I/IGFBP-3 complex has been predicted in the art (Sommer et al., ibid.; Zapf et al., ibid.). However, Applicants have discovered that the IGFI/IGFBP-3 complex can deliver a dose of IGF-I that is surprisingly greater than one skilled in the art would have predicted. Applicants have also have discovered, unexpectedly, that the IGF-I/IGFBP-3 complex prevents other, dose-limiting, side effects of IGF-I administration.

As used herein, "IGF-I" refers to insulin-like growth factor I from any species, including bovine, ovine, porcine and human, in nativesequence or variant form, including but not limited to naturally-occurring allelic variants, and from any source, whether natural, synthetic or recombinant, provided that it will bind IGFBP-3 at the appropriate site. Preferred herein is human native-sequence, mature IGF-I, more preferably without an amino-terminal methionine. More preferably, the native sequence, mature IGF-I is produced recombinantly, for example, as described in PCT publication WO 95/04076.

As used herein, "acid labile subunit" and "ALS" refer to the acidlabile, 84–86 kD, non-IGF-binding subunit of the 125–150 kD ternary complex. ALS is preferably human ALS. ALS may be from any source, including natural, synthetic, or recombinant sources.

"Insulin-like growth factor binding protein 3" (IGFBP-3) is a member of the insulin-like growth factor binding protein family. IGFBP-3 may be from any species, including bovine, ovine, porcine and human, in nativesequence or variant form, including but not limited to naturally-occurring allelic variants. IGFBP-3 can form a binary complex with IGF, and a ternary complex with IGF and the acid labile subunit (ALS). IGFBP-3 may be from any source, whether natural, synthetic or recombinant, provided that it will bind IGF-I and ALS at the appropriate sites.

A "therapeutic composition", as used herein, is defined as comprising IGF-I complexed with its binding protein, IGFBP-3 (IGFI/IGFBP-3 complex). The therapeutic composition may also contain other substances such as water, minerals, carriers such as proteins, and other excipients known to one skilled in the art.

A subject having "insufficient levels of growth hormone" is one who lacks sufficient levels of growth hormone to maintain proper growth and health. Insufficient levels of growth hormone may be found in a number of pathological states, including, but not limited to, dwarfism and hypopituitarism (Bengtsson et al., 1993, "Treatment of Adults with Growth Hormone (GH) Deficiency with Recombinant Human GH" *J Clin.Endocrinol. Metabol.* 76(2): 309–317).

A subject having "growth hormone resistance" is a subject having normal to elevated levels of growth hormone, but who fails to respond to growth hormone. Growth hormone resistance may be found in a number of pathological states, including, but not limited to, Laron type dwarfism, recovery from trauma, bums or injury, malnutrition, severe infection, and AIDS (Ross et al., 1991, "Critically Ill Patients Have High Basal Growth Hormone Levels with Attenuated Oscillatory Activity Associated with Low Levels of Insulin-like Growth Factor-I" *Clin. Endocrinol.* 35: 47–54; Hintz et al., 1978, "Plasma Somatomedin and Growth Hormone Values in Children with Protein-Calorie Malnutrition" *J Pediatr.* 92: 153–156; Dahn et al., 1988, "Insulin-like Growth Factor I Production Is Inhibited in Human Sepsis" *Arch. Surg* 123:1409–1414; Lieberman et al., supra).

Conditions that will benefit from high dose IGF-I therapy are any condition that would benefit from the administration of IGF-I. Such conditions include, but are not limited to: neurological disorders such as amyotrophic lateral sclerosis, Charcot-Marie-Tooth Syndrome, diabetic neuropathy, and drug-induced neuropathy (such as peripheral neuropathy induced by chemotherapeutic agents including vincristine, cisplatin, and the like), and pulmonary disorders such as chronic obstructive pulmonary disease; renal disorders such as glomerulonephritis, glomerulosclerosis, interstitial nephritis, acute tubular necrosis, diabetic nephropathy, autoimmune nephropathy, and acute and chronic renal failure; growth disorders such as growth hormone insufficiency, hypopituitarism, growth hormone resistance and Laron dwarfism; recovery from bodily insults, -such as recovery from trauma, burns, bone fractures or surgery; gastrointestinal disorders such as short bowel syndrome and pancreatic disease; reversal of catabolism in subjects with acquired immune deficiency syndrome (AIDS), cancer cachexia, or steroid-induced catabolism (such as can occur as a result of long term steroid therapy for disorders such as asthma, autoimmune disease, inflammatory bowel disease, immune suppression for organ transplantation, and rheumatoid diseases); bone disorders such as osteoporosis, osteopetrosis, osteogenesis imperfecta, and Paget's disease; reproductive disorders such as hypogonadotropic hypogonadism, male infertility, failure of gamete maturation, and polycystic ovarian disease; and hematopoietic disorders such-as anemia, plasma cell dyscrasias, erythropoietin insensitivity and deficient total hemoglobin.

It is desirable to give high dose IGF-I therapy by administering IGF-I/IGFBP-3 complex to a subject because of the increased efficacy of higher doses.

The method of the invention involves giving a dose of IGF-I/IGFBP-3 complex to a human by parenteral administration. Parenteral administration includes, but is not limited to, intravenous (IV), intramuscular (IM), subcutaneous (SC), intraperitoneal (IP), intranasal, and inhalant routes. IV, IM, SC, and IP administration may be by bolus or infusion, and in the case of SC, may also be by slow release implantable device, including, but not limited to pumps, slow release formulations, and mechanical devices. The formulation, route and method of administration, and dosage will depend on the disorder to be treated and the medical history of the patient. In general, a dose that is administered by subcutaneous injection will be greater than the therapeutically-equivalent dose given intravenously or intramuscularly. A composition comprising equimolar amounts of IGF-I and IGFBP-3 is preferred. Preferably the IGF-I and IGFBP-3 are complexed prior to administration. Preferably, the complex is formed by mixing approximately equimolar amounts of IGF-I and IGFBP-3 dissolved in physiologically compatible carriers such as normal saline, or phosphate buffered saline solution. Most preferably, a concentrated solution of rhIGF-I and a concentrated solution of rhIGFBP-3 are mixed together for a sufficient time to form an equimolar complex.

For parenteral administration, compositions of the complex may be semi-solid or liquid preparations, such as liquids, suspensions, and the like. Physiologically compatible carriers include, but are not limited to, normal saline, serum albumin, 5% dextrose, plasma preparations, and other protein-containing solutions. Optionally, the carrier may also include detergents or surfactants.

The dose of complex to be administered can be readily determined by those skilled in the art, based on the condition to be treated, the severity of the condition, and the patient's medical history. Preferably, when the complex is administered daily, the intravenous or intramuscular dose for a human is about 0.5 mg/kg to 10 mg/kg of body weight per day. More preferably, the daily intravenous or intramuscular dose for a human is about 0.8 mg/kg to 5 mg/kg. Most preferably, the daily intravenous or intramuscular dose for a human is about 1 mg/kg to 3 mg/kg. For subcutaneous administration, the dose is preferably greater than the therapeutically-equivalent dose given intravenously. Preferably, the daily subcutaneous dose for a human is 1 mg/kg to 20 mg/kg.

Trauma and many disease states can lead to reduced levels of growth hormone, which in turn can lead to reduced levels of ALS (Miell et al., 1992, "Administration of Human Recombinant Insulin-like Growth Factor-I to Patients Following Major Gastrointestinal Surgery", *Clin. Endocrinol.* 37: 542–551; Cioffi et al., 1994, "Insulin-like Growth Factor-I Lowers Protein Oxidation in Patients with Thermal Injury" Ann. *Surg.* 220(3): 310–319). Other conditions, such as acquired immune deficiency syndrome (AIDS), can lead to growth hormone resistance, which can also lead to reduced levels of ALS (Lieberman et al., 1994, "Anabolic Effects of Recombinant Insulin-like Growth Factor-I in Cachetic Patients with Acquired Immunodeficiency Syndrome" *J. Clin. Endocrinol. Metabol.* 78(2): 404–410). The daily dose for humans suffering from reduced growth hormone levels or growth hormone resistance, is preferably about 0.3 mg/kg to about 20 mg/kg. More preferably, the daily dose for a human suffering from reduced growth hormone levels or growth hormone resistance is about 0.5 mg/kg to about 10 mg/kg. Most preferably, the daily dose for a human suffering from reduced growth hormone levels or growth hormone resistance is about 0.75 mg/kg to about 5 mg/kg.

Children normally have sufficient levels of growth hormone and are not resistant to growth hormone. However, ALS levels are lower than adult levels (Baxter and Martin, supra). For example, children from zero to one year of age have ALS levels that are reduced by 50% or more when compare to adult ALS levels. Children from one to seven years of age have a ALS levels that are reduced by 30% or more when compared to ALS levels in adults. Thus children from zero to seven years of age are like persons with insufficient levels of growth hormone or growth hormone resistance, in that they have low ALS levels. Preferably, the daily dose of IGF-I/IGFBP-3 complex for a child from zero to one year of age is about 0.3 mg/kg to about 10 mg/kg. Preferably, the daily dose of IGF-I/IGFBP-3 complex for a child from one to seven years of age is about 0.4 mg/kg to about 15 mg/kg.

EXAMPLES

Example 1

Adult male rats were used to test for protection from hypoglycemia by recombinant human (rh) IGF-I/IGFBP-3 complex. The rats were given a single intravenous dose of rhIGF-I or rhIGF-I/IGFBP-3 and monitored for drug pharmacokinetics and any hypoglycemic response. Animals (three per group) were given vehicle alone (control), 0.02, 0.2, 2, or 5 mg/kg rhIGF-I, or 1, 10, 100, or 200 mg/kg rhIGF-I/IGFBP-3 (note that the rhIGF-I/IGFBP-3 doses are the molar equivalents of approximately 0.2, 2, 20, and 40 mg/kg rhIGF-I), then monitored for 72 hours.

Rats were anesthetized and catheters were placed in to the jugular veins. The catheterized animals were allowed to recover for 2 days, then given a single intravenous (IV) bolus injection. Serial blood samples were taken just prior to injection, at 5, 20, and 40 minutes following injection, and at 1, 2, 3, 4, 6, 8, 24, 32, 48, 56, and 72 hours following injection. Serum was harvested from the blood samples and used to assay for drug concentration and blood glucose.

Clinical observations consistent with hypoglycemia (i.e. lethargy/inactivity) were observed in rats receiving a 2 mg/kg or 5 mg/kg dose of IGF-1. Of the rats receiving rhIGF-I/IGFBP-3 complex, only the rats receiving a 200 mg/kg dose showed clinical signs of hypoglycemia. Serum glucose levels also indicated severe hypoglycemia in rats receiving 2 mg/kg or 5 mg/kg IGF-I, showing a reduction of 69% and 71% in serum glucose, respectively. Of the animals receiving rhIGF-I/IGFBP-3 complex, only those receiving 200 mg/kg rhIGF-I/IGFBP-3 displayed any significant reduction in serum glucose levels. Interestingly, 200 mg/kg of rhIGFI/IGFBP-3 complex resulted in a lesser degree of hypoglycemia than either the 2 mg/kg or 5 mg/kg doses of rhIGF-I (FIG. 1).

The doses of IGF-I/IGFBP-3 complex that could be given without induction of hypoglycemia (i.e. up to 100 mg/kg) were substantially greater than the dose predicted to cause hypoglycemia. In rats, a dose of 4.9 mg/kg or greater is predicted to induce hypoglycemia. The results from this study, however, indicate that IGF-I/IGFBP-3 complex can be given at doses over 20 times the expected dose.

Example 2

Adult male cynomologous monkeys were used to test rhIGFI/IGFBP-3 complex pharmacokinetics and for protection from IGF-I's adverse effects. Monkeys (three per dose) were each given a single IV dose of either 2 mg/kg of rhIGF-I or 1, 10, 25, or 100 mg/kg of rhIGF-I/IGFBP-3 (note that the rhIGF-I/IGFBP-3 doses are equivalent to 0.2, 2, 5, and 20 mg/kg rhIGF-I) and monitored for several physiological parameters. Blood samples were taken prior to dosing, at 5, 10, 15, 30, 45, and 60 minutes after dosing, and 2, 4, 8, 1, 24, 48, 72, and 96 hours after dosing. Serum was harvested from the blood samples and used to determine drug concentration and serum levels of glucose, phosphate, and sodium. Animals were also closely monitored for signs of hypoglycemic shock during and after dosing.

Monkeys were placed into primate metabolism chairs prior to administration of drug, and kept in the chairs for four hours postadministration. Drug was administered as an IV bolus via an indwelling catheter placed either in the cephalic or saphenous vein.

Animals receiving 2 mg/kg rhIGF-I showed clinical signs of severe, life-threatening hypoglycemia, and required the oral administration of glucose. Animals receiving 100 mg/kg rhIGF-I/IGFBP-3 also showed clinical signs of severe hypoglycemia. Assays of serum glucose levels also demonstrated significant reductions in serum glucose in animals receiving 2 mg/kg IGF-I and 25 and 100 mg/kg rhIGF-I/IGFBP-3. However, the reduction in serum glucose observed in animals receiving rhIGF-I/IGFBP-3 complex was less severe than that seen in animals receiving rhIGF-I alone (74% reduction versus 90% reduction in serum glucose).

Serum phosphate and serum sodium levels were also measured in the blood samples from this experiment. Some animals receiving rhIGF-I showed abnormalities in serum phosphate and serum sodium levels. One of the three animals receiving 2 mg/kg rhIGF-I showed severe acute hypophosphatemia, with a serum phosphorus level of 1.4 mg/dL (severe hypophosphatemia is defined as less than 1.5 mg/dL; *The Merck Manual of Diagnosis and Therapy*, 16th ed., Berkow, R., ed., Merck Research Laboratories, Rahway, N.J., 1992). Hypophosphatemia can cause muscle seizures and cardiac abnormalities, and was the cause of a Food and Drug Administration-imposed dosage limitation for IGF-I (Malozowski and Stadel, 1994, "Risks and Benefits of Insulin-like Growth Factor" *Ann. Int. Med.* 121(7): 549). No hypophosphatemia was observed in blood samples from animals receiving rhIGF-I/IGFBP-3, indicating that rhIGF-I/IGFBP3 complex prevents IGF-1-associated hypophosphatemia.

All of the animals receiving rhIGF-I also showed significantly increased levels of serum sodium, or hypematreniia. Hypematremia is defined as serum sodium greater than 150 meq/liter (*Current Emergency Diagnosis and Treatment*, 4 ed., Saunders, C. E. and Ho, M. T., eds. Lange Medical Publications, 1992) Each of these animals had serum sodium levels in excess of 150 meq/liter at least three of the post-dosing time points (peak levels were from 163 to 168 meq/L). In contrast, animals receiving IGF-I/IGFBP-3 never had hypematremic serum sodium levels at any post-dosing time point. Hypematremia may be the cause of the edema observed in patients receiving IGF-I (Jabri et al., 1994, "Adverse Effects of Recombinant Human Insulin-like Growth Factor I in Obese Insulin-resistant Type-II Diabetic Patients", *Diabetes* 43: 369–374). IGF-I-induced hypematremia may also be source of edema and carpal tunnel syndrome associated with administration of human growth hormone (Ogle et al., 1992, "Renal Effects of Growth Hormone. II. Electrolyte Homeostasis and Body Composition", *Pediatr. NephroL* 6: 483–489; Cohn et al., 1993, "Carpal Tunnel Syndrome and Gynaecomastia During Growth Hormone Treatment of Elderly Men with Low Circulating IGF-I Concentrations", *Clin. Endocrinol.* 39: 417–425). None of the animals receiving rhIGFI/IGFBP-3 complex showed hypematrernia, indicating that rhIGF-I/IGFBP-3 complex prevents IGF-1-associated hypematremia.

Example 3

Male Sprague-Dawley rats were used to test the pharmacokinetic profile of rhIGF-I/IGFBP-3 complex administered by different routes. Rats were assorted into three groups, which received 10 mg/kg of rhIGF-I/IGFBP-3 complex by either intravenous (IV), intramuscular (IM), or subcutaneous (SC) administration. Blood samples were taken prior to rhIGF-I/IGFBP-3 complex administration (and designated 0 time), and at 20 and 40 minutes, and 1, 2, 3, 4, 6, 8, 24, 32, 48, 56, 72, 80, and 96 hours after administration. Serum was harvested from the blood samples and used to test for serum levels of rhIGF-I or IGFBP-3, using a sandwich IRMA assay specific for human IGF-I (Diagnostic Systems Laboratories, Inc., Webster, Tex.) or an RIA assay for IGFBP-3 (Endocrine Sciences, Calabasas Hills, Calif.).

A total of 18 rats were used in this experiment. The rats were randomly assorted to three groups of six rats each. Three days before administration of the rhIGF-I/IGFBP-3 complex, test animals were anesthetized and a cannula was implanted into the jugular vein. Intravenous administration was accomplished using the cannula. Subcutaneous injections were made into the dorsal pelvic region. Intramuscular administration was by injection into the caudal thigh muscle.

Figure 2:
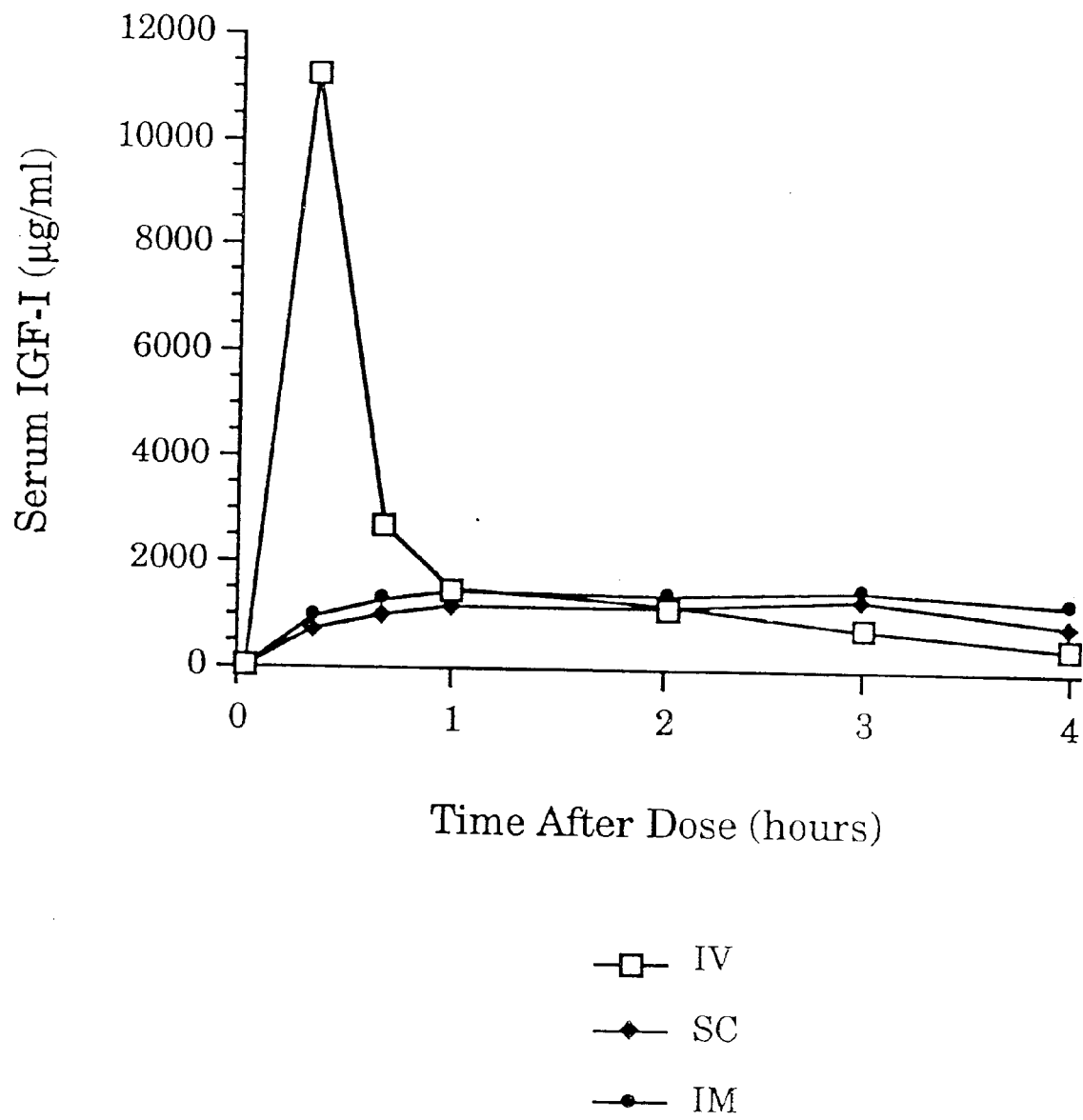
FIG. 2 shows serum levels of human rhIGF-I in rats following intravenous (IV), intramuscular (IM) or subcutaneous (SC) bolus administration. Open squares indicate IV; filled diamonds indicate SC; filled circles indicate IM. Serum samples were assayed using an IRMA assay which is specific for human IGF-I.

As shown in FIG. 2, SC and IM administration resulted in reduced peak concentrations and delayed concentration maxima, as compared to IV administration. In IV treated animals, the highest measured concentration of IGF-I/IGFBP-3 complex was at 20 minutes. In comparison, the highest measured concentrations in SC and IM injected animals were at 3 hours.

SC and IM administration also resulted in considerably lower peak concentrations of IGF-I/IGFBP-3 complex as compared to IV administration. The maximum measured concentration in IV treated animals was nearly 10 fold greater than the peak concentrations in SC and IM injected animals (11253±348 µg/ml versus 1290±456 and 1452±111 µg/ml, respectively).

Bioavailability was substantially reduced in SC injections, but not IM injections. SC bioavailability, calculated as the ratio of the area under the serum concentration vs. time curve following SC administration to that following IV administration, was approximately 50%, while IM (calculated in a similar fashion) bioavailability was approximately 95%. These bioavailability data suggest that dose of IGF-I/IGFBP-3 given SC should be doubled for the same therapeutic effect as IV or IM administered IGF-I/IGFBP-3.

The patents, patent applications, and publications cited throughout the disclosure are incorporated herein by reference in their entirety.

The present invention has been detailed both by direct description and by example. Equivalents and modifications of the present invention will be apparent to those skilled in the art, and are encompassed within the scope of the invention.

We claim:

1. A method for providing high dose IGF-I therapy without inducing clinically significant hypoglycemia, comprising administering a 1 milligram per kilogram to 20 milligrams per kilogram dose of IGFI/IGFBP-3 complex to a human, wherein said dose is administered by subcutaneous infusion or slow release implantable device.

2. The method of claim 1, wherein said dose is 1 milligram per kilogram to 3 milligrams per kilogram.

* * * * *